United States Patent [19]

Gordon

[11] 4,109,084
[45] Aug. 22, 1978

[54] THIOOXIME CEPHALOSPORIN DERIVATIVES

[75] Inventor: Eric M. Gordon, West Trenton, N.J.

[73] Assignee: E. R. Squibb & Sons, Inc., Princeton, N.J.

[21] Appl. No.: 748,425

[22] Filed: Dec. 8, 1976

[51] Int. Cl.² .................. C07D 501/26; C07D 501/48
[52] U.S. Cl. ...................................... 544/29; 544/24; 544/26; 260/239.1
[58] Field of Search .............. 260/243 C; 544/24, 29

[56] References Cited
U.S. PATENT DOCUMENTS

| | | | |
|---|---|---|---|
| 3,907,788 | 9/1975 | Nudelman | 260/243 C |
| 3,919,207 | 11/1975 | Terao et al. | 260/243 C |

*Primary Examiner*—Donald G. Daus
*Assistant Examiner*—David E. Wheeler
*Attorney, Agent, or Firm*—Lawrence S. Levinson; Merle J. Smith; Stephen B. Davis

[57] ABSTRACT

Compounds of the formula

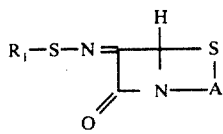

wherein A is

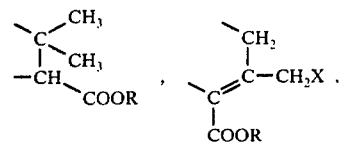

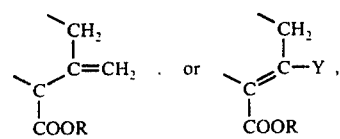

R is hydrogen, lower alkyl, benzyl, p-methoxybenzyl, p-nitrobenzyl, diphenylmethyl, tri(lower alkyl)silyl, lower alkoxymethyl, 2,2,2-trichloroethyl,

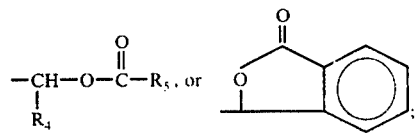

Y is halogen or lower alkoxy; $R_1$ is lower alkyl, phenyl, or substituted phenyl; and X is hydrogen, lower alkanoyloxy,

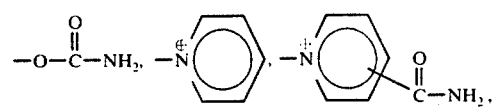

or certain heterothio groups; $R_4$ is hydrogen or lower alkyl; $R_5$ is lower alkyl; are disclosed. These compounds, particularly the free acids, possess the useful pharmacological property of inhibiting β-lactamase enzymes as well as being useful as intermediates, particularly where R is a readily cleavable ester, in the preparation of antibacterially active 6α-methoxy penicillins and 7α-methoxy cephalosporins.

12 Claims, No Drawings

THIOOXIME CEPHALOSPORIN DERIVATIVES

BACKGROUND OF THE INVENTION

Welch, J. Org. Chem., Vol. 41, p. 2220-2222, discloses reacting 6-aminopenicillanic acid (6-APA) with an arylsulfenyl chloride under aqueous conditions to yield a mixture of an aryl sulfenamide and a diarylsulfenimide 6-substituted penicillin.

Nudelman in U.S. Pat. No. 3,907,788 discloses reacting 7-aminocephalosporanic acid (7-ACA) with an equimolar amount of a sulfenyl derivative to yield a 7-sulfenamido cephalosporin.

The combination of an active antibacterial agent and an agent having β-lactamase inhibition are taught in U.S. Pat. Nos. 3,624,225, 3,867,538, and 3,952,094.

Various acylated 7α-methoxy cephalosporins and 6α-methoxy penicillins are disclosed as possessing useful antibacterial activity as note for example U.S. Pat. Nos. 3,775,410, 3,780,031, 3,780,033, 3,780,037, 3,843,641, 3,920,639, 3,960,845, 3,978,651, etc.

Also, 7-amino-7-substituted thio-cephalosporins and 6-amino-6-substituted thio-penicillins are disclosed in U.S. Pat. Nos. 3,840,533 and 3,855,233.

SUMMARY OF THE INVENTION

This invention relates to new thiooxime cephalosporin and penicillin derivatives of the formula

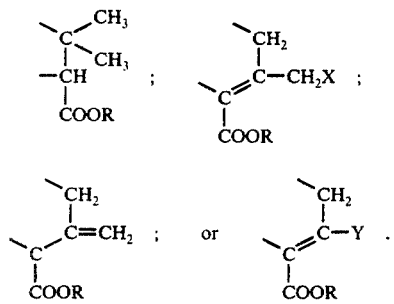

A represents

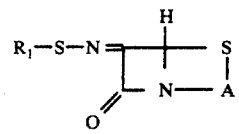

R represents hydrogen, lower alkyl, benzyl, p-methoxybenzyl, p-nitrobenzyl, diphenylmethyl 2,2,2-trichloroethyl, tri(lower alkyl)silyl, lower alkoxymethyl,

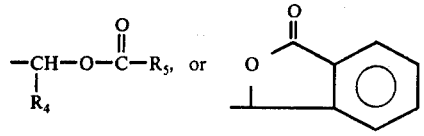

Y is halogen or lower alkoxy.

$R_1$ represents lower alkyl, phenyl, or substituted phenyl.

X represents hydrogen, lower alkanoyloxy,

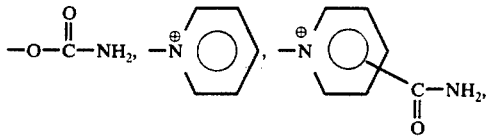

or certain heterothio groups.

$R_4$ is hydrogen or lower alkyl.
$R_5$ is lower alkyl.

Also disclosed are methods of converting the compounds of formula I to antibacterially active 7-acyl-7α-methoxy cephalosporins and 6-acyl-6α-methoxy penicillins.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 4 carbon atoms. Examples of the type of groups contemplated are methyl, ethyl, n-propyl, isopropyl, t-butyl, etc. The lower alkoxy groups include such lower alkyl groups attached to an oxygen, e.g., methoxy, ethoxy, propoxy, etc.

The term halogen employed in the definition of the variable Y is meant to include the four common halogens, e.g. chlorine, bromine, fluorine or iodine, with chlorine being preferred.

The substituted phenyl groups include a single substituent selected from halogen (preferably chlorine or bromine), lower alkyl of 1 to 4 carbons (preferably methyl or ethyl), and lower alkoxy of 1 to 4 carbons (preferably methoxy or ethoxy).

Lower alkanoyloxy refers to a group of the formula

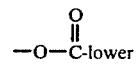

alkyl wherein lower alkyl is of 1 to 4 carbons, preferably wherein lower alkyl is methyl.

The heterothio groups are

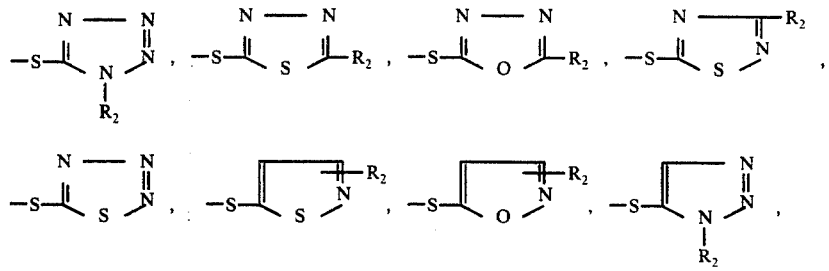

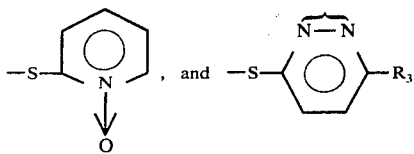

wherein R₂ is hydrogen or lower alkyl of 1 to 4 carbons (preferably methyl or ethyl) and R₃ is hydrogen, lower alkyl of 1 to 4 carbons (preferably methyl or ethyl), methoxy, hydroxy, or halogen (preferably chlorine).

The compounds of formula I wherein A, Y, and R₁ are as defined above; X is hydrogen, lower alkanoyloxy,

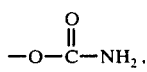

or heterothio; and R is hydrogen, lower alkyl, benzyl, p-methoxybenzyl, p-nitrobenzyl, diphenylmethyl, tri(-lower alkyl)silyl, lower alkoxymethyl or 2,2,2-trichloroethyl; are prepared by reacting a 6-aminopenicillin or 7-aminocephalosporin of the formula

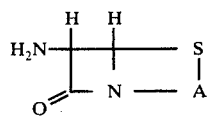

with a halosulfenyl compound of the formula

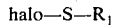                      (III)

wherein halo is preferably chlorine or bromine. This reaction is performed in an inert non-aqueous solvent such as methylene chloride, chloroform, ethyl acetate, dimethylformamide, tetrahydrofuran, etc., with at least a molar excess, preferably 2 to 4 equivalents, of the sulfenyl compound of formula III. The reaction is performed at a temperature of from about −30° C to about 30° C for from about 1 to about 24 hours. Preferably one or more acid scavengers such as propylene oxide, butylene oxide, pyridine, tri(lower alkyl)-amine, or crushed molecular sieves are employed in the reaction and the reaction is performed under an inert atmosphere, e.g. argon or nitrogen. When R is hydrogen, the compound of formula II is preferably converted to its trimethylsilyl ester before reaction with the sulfenyl compound.

The compounds of formula I wherein X is pyridinium or carbamoyl substituted pyridinium are prepared by reacting a compound of the formula (or its sodium salt)

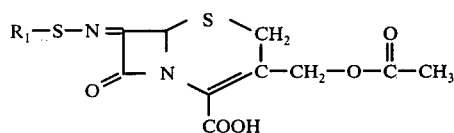

with pyridine or carbamoyl substituted pyridine in a polar solvent such as water and in the presence of a catalyst such as an alkali metal thiocyanate. U.S. Pat. No. 3,792,047 and German Offenlegungsschrift No. 2,234,280 both disclose methods for reacting a cephalosporin so as to replace an acetoxy group with a pyridinium group.

Also, the compounds of formula I wherein X is heterothio can be prepared by reacting the compound of formula Ia with a mercaptan of the formula

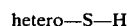                      (IV)

or an alkali metal (preferably sodium) mercaptan salt of the formula

                      (V)

Methods for displacing the acetoxy group of a cephalosporin by a heterothio group are taught in various U.S. Pat. Nos. including 3,855,213; 3,890,309; 3,892,737; etc.

The compounds of formula I wherein R is

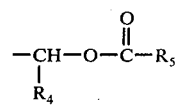

may be obtained by treating the compound of formula II wherein R is hydrogen either before or after the reaction with the sulfenyl compound with one or two moles of a compound of the formula

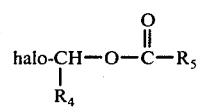                      (VI)

wherein halo is chlorine or bromine in an inert solvent such as dimethylformamide at or below ambient temperature.

Similarly, the compounds of formula I wherein R is

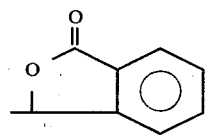

are prepared by treating the compound of formula II wherein R is hydrogen either before or after the reaction with the sulfenyl compound of formula III with a compound of the formula

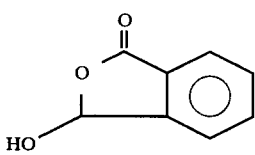                      (VII)

as taught by Ferres et al. in U.S. Pat. No. 3,860,579.

The thiooxime compounds of formula I particularly wherein R is a readily cleavable ester group such as t-butyl, benzyl, p-methoxybenzyl, p-nitrobenzyl, diphenylmethyl, and 2,2,2-trichloroethyl are valuable as intermediates in the preparation of various antibacterially active 7-acyl-7α-methoxy cephalosporins and 6-acyl-6α-methoxy penicillins by several routes.

For example, the thiooxime compound of formula I can be reacted with a tri(lower alkyl)phosphine, a tri(phenyl) or a tri(substituted phenyl)phosphine, preferably triphenylphosphine, followed by treatment with an acid catalyst such as silica gel to yield the 7β-amino-7α-substituted thio cephalosporin or 6β-amino-6α-substituted thio penicillin of the formula

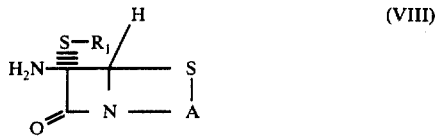

wherein $R_1$ and A are as defined above. The reaction between the thiooxime of formula I and the phosphine is performed in an inert solvent such as methylene chloride, chloroform, ethylacetate, dimethylformamide, tetrahydrofuran, etc., at about 0° to about 80° C for from about 1 to about 24 hours. The reaction is preferably performed under an inert atmosphere such as nitrogen or argon.

The resulting compound of formula VIII can then be acylated according to known procedures to yield the compounds of the formula

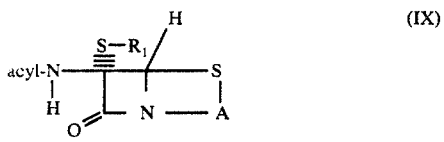

which are then treated with a metal salt such as mercuric acetate, mercuric chloride, silver tetrafluoroborate, etc., in the presence of methanol as taught in German Offenlegungsschrift No. 2,360,945 of Dolfini et al. and by Applegate et al. in J. Org. Chem., Vol. 39, p. 2794–2796 to yield the corresponding acylated 7α-methoxy cephalosporins or 6α-methoxy penicillins. The ester protecting group (i.e. R is t-butyl, benzyl, p-methoxybenzyl, p-nitrobenzyl, diphenylmethyl, 2,2,2-trichloroethyl) can then be removed according to known methods to yield the final compounds in the free acid form.

Alternatively, the compound of formula VIII can be treated with a metal salt such as mercuric chloride in the presence of methanol as taught in Belgium Pat. No. 811,314 and by Jen et al. in J. Org. Chem., Vol. 38, p. 2857–2859 to yield the corresponding 7β-amino-7α-methoxy cephalosporin or 6β-amino-6α-methoxy penicillin of the formula

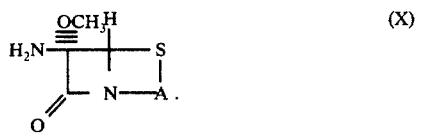

Acylation followed by the removal of the ester protecting group according to known procedures yields the desired final products.

Also, it has been discovered that the thiooximes of formula I can be reacted so as to yield the compound of formula X directly thus obviating the need to proceed via the intermediate of formula VIII. This reaction can be performed by forming a solution of the thiooxime of formula I in an inert solvent such as methylene chloride, ethyl acetate, chloroform, dimethylformamide, tetrahydrofuran, etc., and adding under an inert atmosphere a tri(lower alkyl)phosphine, or a tri(phenyl)phosphine, or a tri(substituted phenyl)phosphine, preferably triphenylphosphine. The reaction mixture is kept at a temperature of from about 0° to about 80° C for from about 1 to about 24 hours with stirring. A metal catalyst such as mercuric acetate, mercuric chloride, silver tetrafluoroborate, silver acetate, silver nitrate, silver perchlorate, lead acetate, or thallium acetate, preferably mercuric acetate, mercuric chloride, or silver tetrafluoroborate, and methanol are added to the reaction mixture. After about 1 to about 4 hours, the reaction mixture is concentrated and the product of formula X is either isolated by conventional procedures or acylated directly to yield the desired 6-acyl-6α-methoxy penicillin or 7-acyl-7α-methoxy cephalosporin. Alternatively, the thiooxime solution, phosphine, metal catalyst and methanol can be combined into a reaction mixture at one time. After about 4 to about 8 hours at from about 0° to about 80°, the reaction mixture is concentrated and the product of formula X is either isolated or acylated directly.

The thiooxime compounds of formula I particularly those wherein R is hydrogen, lower alkoxymethyl,

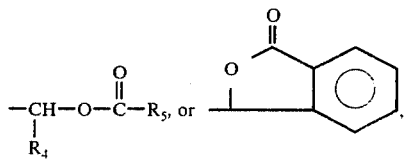

especially those wherein R is hydrogen, possess the useful pharmacological property of inhibiting β-lactamase enzymes. Thus, these compounds can be combined with known antibacterial agents which are susceptible to attack by β-lactamase enzymes and enhance the antibacterial activity of these known agents. Examples of such known antibacterial agents include penicillins such as penicillin G, penicillin V, ampicillin, amoxycillin, and epicillin, preferably ampicillin, and cephalosporins such as cephradine, cephalexin, cefazolin, cefoxitin, cefaloridine, cephaloglycin, and cefamandole, preferably cephradine. The thiooxime is present at from about 1% to about 90% by weight of the antibacterial combination. Since a unit dose of most antibacterial agents for a 70 kg. mammal contains from about 250 mg. to about 2 g. of active ingredient, the thiooxime will be present at from about 2.5 mg. to about 1.8 g. in the unit dose.

The thiooxime and active antibacterial agent are formulated into a composition along with a pharmaceutically acceptable carrier and other ingredients according to accepted pharmaceutical practice. The composition is formulated so as to be administered orally or parenterally depending upon the mode of administration best suited for the particular active antibacterial agent. Thus, a suitable injectable composition is a dry blend of the antibacterial agent, thiooxime, and sodium carbonate which is then reconstituted with water prior to administration.

The following examples are illustrative of the invention. All temperatures are expressed in degrees centigrade.

EXAMPLE 1

7-[[(4-Methylphenyl)thio]imino]-3-[(acetyloxy)methyl]-8-oxo-5-thia-1-azabicyclo[4.2.0]oct-2-ene-2-carboxylic acid A mixture of 4 g. (16.7 mmol.) of 7β-amino-3-[(acetyloxy)-methyl]-8-oxo-5-thia-1-azabicyclo[4.2.0]oct-2-ene-2-carboxylic acid (i.e. 7-ACA), 8.3 ml. (33.4 mmol.) of bis(trimethylsilyl)-acetamide, pulverized molecular sieves (4A, ≃1000 beads), 16 ml. of propylene oxide, and 320 ml. of methylene chloride is stirred at 26° for 1.5 hours under a nitrogen atmosphere. The reaction mixture is cooled to 0° and 10.07 g. (66.8 mmol.) of p-toluenesulfenyl chloride is added dropwise over 20 minutes. The mixture is stirred at ambient temperature for three hours, and then poured into 5% sodium bicarbonate solution. The inorganic layer is acidified by the addition of 1N HCl and extracted twice with 200 ml. of ethyl acetate. The combined organic extracts are dried over $Na_2SO_4$, and then concentrated under reduced pressure to a tan foam. The foam is triturated with ethyl ether to yield 1.75 g. of a tan crystalline material. Recrystallization without heating from methanol/acetone/ether/hexane affords pure pale yellow crystalline 7-[[(4-methylphenyl)thio]imino]-3-[(acetyloxy)methyl]-8-oxo-5-thia-1-azabicyclo[4.2.0]oct-2-ene-2-carboxylic acid; m.p. 204°-205.5°.

EXAMPLE 2

3-Methyl-7-[[(4-methylphenyl)thio]imino]-8-oxo-5-thia-1-azabicyclo[4.2.0]oct-2-ene-2-carboxylic acid A mixture of 5 g. (23.3 mmol.) of 7β-amino-3-methyl-8-oxo-5-thia-1-azabicyclo[4.2.0]oct-2-ene-2-carboxylic acid (i.e. 7-ADCA), 9.5 g. (46.6 mmol.) of bis(trimethylsilyl)-acetamide, pulverized molecular sieves (4A, ≃1000 beads), 10 ml. of propylene oxide and 200 ml. of methylene chloride is stirred at 26° for 1.5 hours under a nitrogen atmosphere. The reaction mixture is cooled to 0° and 14.1 g. (88.5 mmol.) of p-toluenesulfenyl chloride is added dropwise over 20 minutes. The mixture is stirred at ambient temperature for three hours and then poured into 5% sodium carbonate solution. Bright yellow crystals form and are removed by filtration. The filter cake is washed with 8% salt solution and dried under a vacuum. Recrystallization from methanol/ethyl acetate yields a pure sample of 3-methyl-7-[[(4-methylphenyl)thio]-imino]-8-oxo-5-thia-1-azabicyclo[4.2.0]oct-2-ene-2-carboxylic acid; m.p. 186°-187°.

EXAMPLE 3

7-[[(4-Methylphenyl)thio]imino]-3-[[(1-methyl-1H-tetrazol-5-yl)-thio]methyl]-8-oxo-5-thia-1-azabicyclo[4.2.0]oct-2-ene-2-carboxylic acid A mixture of 5 g. (15.9 mmol.) of 7β-amino-3-[[(1-methyltetrazol-5-yl)thio]methyl]-8-oxo-5-thia-1-azabicyclo[4.2.0]-oct-2-ene-2-carboxylic acid, 7.12 g. (34.9 mmol.) of bis(trimethylsilyl)acetamide, pulverized molecular sieves (4A, ≃1000 beads), 20 ml. of propylene oxide, and 400 ml. of methylene chloride is stirred at 26° for 1.5 hours under a nitrogen atmosphere. The reaction is cooled to 0° and 10.1 g. (63.6 mmol.) of p-toluenesulfenyl chloride is added dropwise over 20 minutes. The mixture is stirred at ambient temperature for three hours and then filtered. The filtrate is extracted twice with 100 ml. of a 5% sodium bicarbonate solution. The aqueous extracts are combined, acidified to pH 2.3 by the addition of HCl, and extracted twice with 150 ml. of ethyl acetate. The organic extracts are combined, dried ($Na_2SO_4$), and concentrated under reduced pressure to a brownish yellow solid. Trituration with ether followed by hexane affords a light tan solid; NMR ($CDCl_3$) δ 2.33 (S, 3H), 3.70 (S, 2H), 3.86 (S, 3H), 4.40 (S, 2H), 5.25 (S, 1H), 7.26 (M, 4H); I.R. (KBr) 1770, 1715 $cm^{-1}$.

EXAMPLES 4-22

Following the procedures of examples 1 to 3 but employing the 7β-amino cephalosporanic acid shown in Col. I and the sulfenyl chloride shown in Col. II, one obtains the thiooxime shown in Col. III.

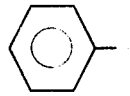
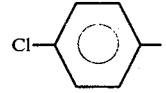
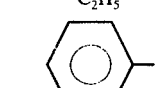

| Ex. | X | $R_1$ |
|---|---|---|
| 4 | 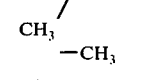 | $-CH_3$ |
| 5 | $-H$ | 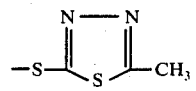 |
| 6 | 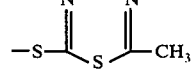 | 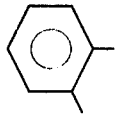 |
| 7 | $-H$ | $-C_2H_5$ |
| 8 | 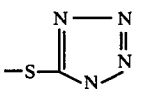 | 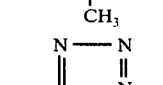 |
| 9 | -S—⟨tetrazole⟩—$CH_3$ | $-CH_3$ |
| 10 | -S—⟨tetrazole⟩—$CH_3$ | ⟨o-tolyl⟩ |
| 11 | -S—⟨N-methyltetrazole⟩ | $-CH_3$ |
| 12 | -S—⟨N-methyltetrazole⟩ | $-n-C_3H_7$ |

-continued

| | Col. I | Col. II |
|---|---|---|
| | (7-ACA structure with CH₂X) | R₁—S—Cl |
| | Col. III | |
| | (thiooxime structure with R₁—S—N=, CH₂X) | |

| Ex. | X | R₁ |
|---|---|---|
| 13 | -S-(1-methyl-tetrazolyl) | phenyl |
| 14 | -S-(1H-tetrazolyl) | -t-C₄H₉ |
| 15 | -S-(5-methyl-1,3,4-oxadiazolyl) | phenyl |
| 16 | -S-(5-ethyl-1,3,4-oxadiazolyl) | 3-OC₂H₅-phenyl, —CH₃ |
| 17 | -S-(4-methyl-thiadiazolyl) | 2-Br-phenyl |
| 18 | -S-(1,3,4-thiadiazolyl) | 4-H₃CO-phenyl |
| 19 | -S-(3-methyl-isothiazolyl) | —C₂H₅ |
| 20 | -S-(4-methyl-isoxazolyl) | phenyl |
| 21 | -S-(1H-triazolyl) | 4-H₃C-phenyl |
| 22 | -S-(1-methyl-triazolyl) | —CH₃ |

EXAMPLE 23

3-Methylene-7-[[(4-methylphenyl)thio]imino]-8-oxo-5-thia-1-azabicyclo[4.2.0]octane-2-carboxylic acid Following the procedure of example 1 but substituting 7β-amino-3-methylene-8-oxo-5-thia-1-azabicyclo[4.2.0]octane-2-carboxylic acid for the 7-ACA, one obtains 3-methylene-7-[[(4-methylphenyl)thio]imino]-8-oxo-5-thia-1-azabicyclo[4.2.0]-octane-2-carboxylic acid.

Similarly, by employing the sulfenyl compounds shown in Col. II of examples 4 to 22 in the above procedure other compounds within the scope of the invention are obtained.

EXAMPLE 24

3-Chloro-7-[[(4-methylphenyl)thio]imino]-8-oxo-5-thia-1-azabicyclo[4.2.0]oct-2-ene-2-carboxylic acid Following the procedure of example 1 but substituting 7β-amino-3-chloro-8-oxo-5-thia-1-azabicyclo[4.2.-0]oct-2-ene-2-carboxylic acid for the 7-ACA, one obtains 3-chloro-7-[[(4-methylphenyl)thio]imino]-8-oxo-5-thia-1-azabicyclo[4.2.0]oct-2-ene-2-carboxylic acid.

EXAMPLES 25-35

Following the procedure of example 24 but employing the 3-halo or alkoxy cephalosporin shown in Col. I and the sulfenyl chloride shown in Col. II, one obtains the thiooxime shown in Col. III.

| | Col. I | Col. II |
|---|---|---|
| | (cephalosporin structure with C—Y) | R₁—S—Cl |
| | Col. III | |
| | (thiooxime structure with R₁—S—N=, C—Y) | |

| Ex. | Y | R₁ |
|---|---|---|
| 25 | Cl | phenyl |
| 26 | Cl | —CH₃ |
| 27 | Br | 4-H₃C-phenyl |
| 28 | Br | —C₂H₅ |
| 29 | I | 4-H₃C-phenyl |
| 30 | F | —n-C₃H₇ |
| 31 | —OCH₃ | 4-H₃C-phenyl |
| 32 | —OC₂H₅ | 3-H₃CO-phenyl |
| 33 | —OCH₃ | 4-Cl-phenyl |

-continued

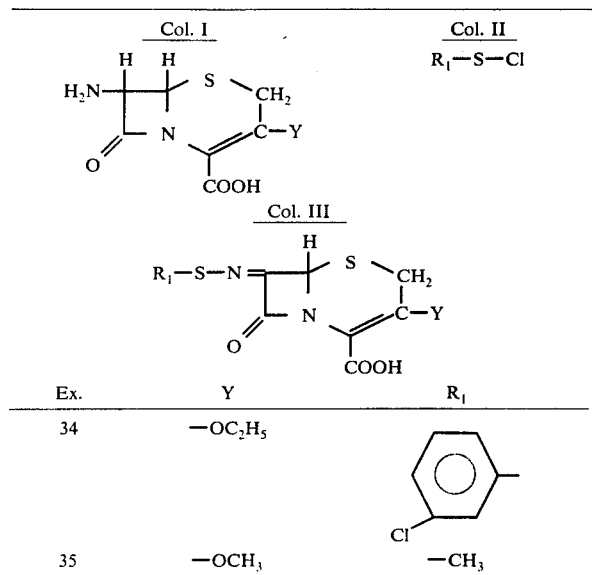

| Ex. | Y | R₁ |
|---|---|---|
| 34 | —OC₂H₅ | (3-chlorophenyl) |
| 35 | —OCH₃ | —CH₃ |

EXAMPLE 36

6-[[(4-Methylphenyl)thio]imino]-3,3-dimethyl-7-oxo-4-thia-1-azabicyclo[3.2.0]heptane-2-carboxylic acid Following the procedure of example 1 but substituting 6β-amino-3,3-dimethyl-7-oxo-4-thia-1-azabicyclo[3.2.0]-heptane-2-carboxylic acid (i.e. 6-APA) for the 7-ACA one obtains 6-[[(4-methylphenyl)thio]imino]-3,3-dimethyl-7-oxo-4-thia-1-azabicyclo[3.2.0]heptane-2-carboxylic acid.

Also, by employing the sulfenyl chlorides of Col. II of examples 4 to 22 within the above procedure other 6-substituted thiooxime penicillins are obtained.

EXAMPLE 37

3-[[4-(Aminocarbonyl)pyridino]methyl]-7-[[(4-methylphenyl)-thio]imino]-8-oxo-5-thia-1-azabicyclo[4.2.0]oct-2-ene-2-carboxylic acid An aqueous solution of the 7-[[(4-methylphenyl)thio]imino]-3-[(acetyloxy)methyl]-8-oxo-5-thia-1-azabicyclo[4.2.0]-oct-2-ene-2-carboxylic acid from example 1 and sodium bicarbonate is lyophilized to yield the sodium salt. An aqueous mixture of this sodium salt, 4-pyridinecarboxamide, and potassium thiocyanate is heated at 50° for 24 hours. The resulting solution is treated by chromatographic means to separate out the 3-[[(4-aminocarbonyl)pyridino]methyl]-7-[[(4-methylphenyl)thio]-imino]-8-oxo-5-thia-1-azabicyclo[4.2.0]oct-2-ene-2-carboxylic acid.

EXAMPLES 38–46

Following the procedure of Example 37 but employing the thiooxime shown in Col. I and the pyridine compound shown in Col. II, one obtains the product shown in Col. III.

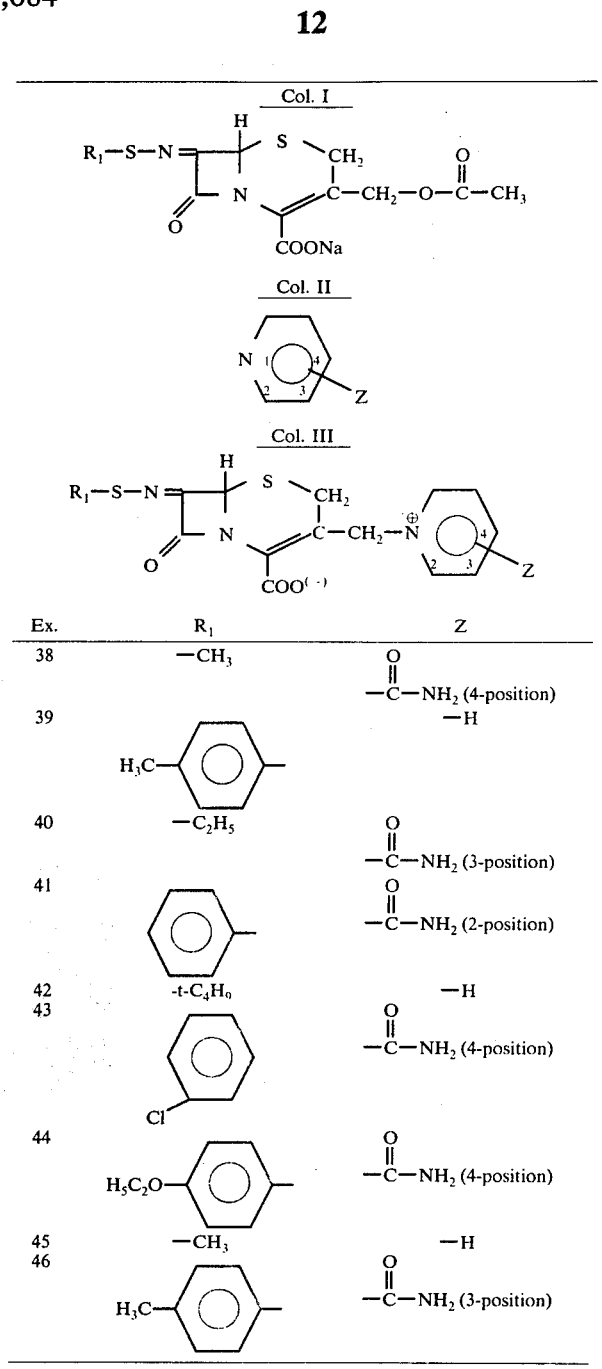

| Ex. | R₁ | Z |
|---|---|---|
| 38 | —CH₃ | —C(O)—NH₂ (4-position) |
| 39 | (4-methylphenyl) | —H |
| 40 | —C₂H₅ | —C(O)—NH₂ (3-position) |
| 41 | (phenyl) | —C(O)—NH₂ (2-position) |
| 42 | -t-C₄H₉ | —H |
| 43 | (4-chlorophenyl) | —C(O)—NH₂ (4-position) |
| 44 | (4-ethoxyphenyl) | —C(O)—NH₂ (4-position) |
| 45 | —CH₃ | —H |
| 46 | (4-methylphenyl) | —C(O)—NH₂ (3-position) |

EXAMPLE 47

7-[[(4-Methylphenyl)thio]imino]-3-[[(1-oxopyridazin-3-yl)thio]-methyl]-8-oxo-5-thia-1-azabicyclo[4.2.0]oct-2-ene-2-carboxylic acid An aqueous solution of the 7-[[(4-methylphenyl)thio]-imino]-3-[(acetyloxy)methyl]-8-oxo-5-thia-1-azabicyclo[4.2.0]-oct-2-ene-2-carboxylic acid from example 1 and sodium bicarbonate is lyophilized to yield the sodium salt. The sodium salt is dissolved in a mixture of acetone:water (1:1) and 1-oxopyridazine-3-thiol, sodium salt is added under a nitrogen atmosphere. The solution is heated at 60° for several hours, diluted with water, and acidified to yield 7-[[(4-methylphenyl)thio]imino]-3-[[(1-oxopyridazin-3-yl)thio]methyl]-8-oxo-5-thia-1-azabicyclo[4.2.0]-oct-2-ene-2-carboxylic acid.

EXAMPLES 48-62

Following the procedure of Example 47 but employing the thiooxime shown in Col. I and the heterothio compound shown in Col. II, one obtains the products shown in Col. III.

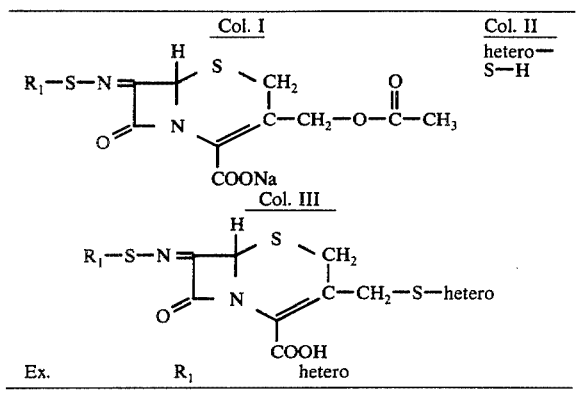

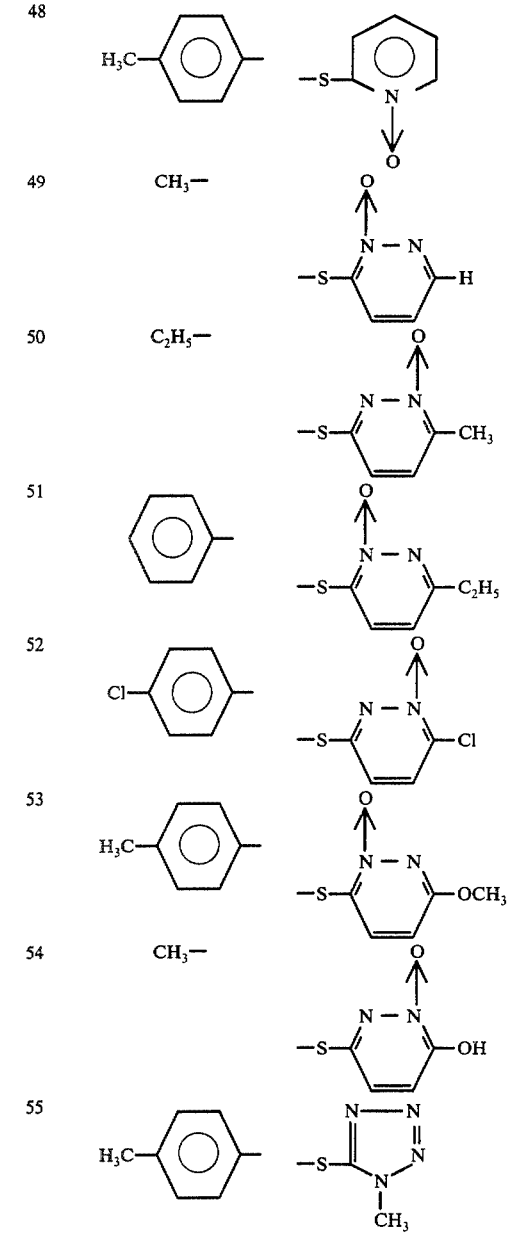

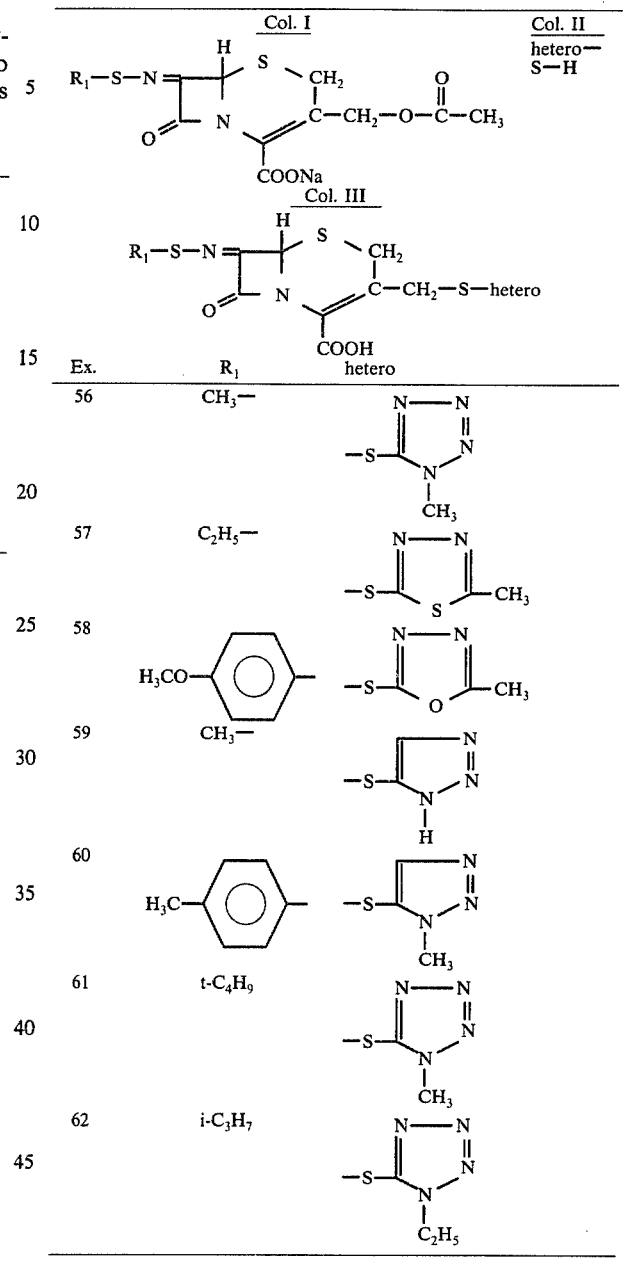

EXAMPLE 63

7β-Amino-7α-[(4-methylphenyl)thio]-3-[[(1-methyl-1H-tetrazol-5-yl)thio]methyl]-8-oxo-5-thia-1-azabicyclo-[4.2.0]oct-2-ene-2-carboxylic acid, diphenylmethyl ester (a)

7-[[(4-Methylphenyl)thio]imino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 7.14 g. (45 mmol.) of p-toluenesulfenyl chloride in 50 ml. of dry methylene chloride is added dropwise with stirring under a nitrogen atmosphere to a cold solution (0°) of 7 g. (14.15 mmol.) of 7β-amino-3-[[(1-methyl-1H-tetrazol -5-yl)thio]methyl]-8-oxo-5-thia-1-azabicyclo[4.2.0]-oct-2-ene-2-carboxylic acid, diphenylmethyl ester in 600 ml. of dry methylene chloride and 60 ml. of propylene oxide also containing 50 g. of crushed molecular sieves (4A). The reaction mixture is stirred, and the temperature allowed to rise to 26° over a three hour period. The resulting mixture is filtered and the filtrate is concentrated to an oil under reduced pressure. Crystallization from methylene chloride/ethyl ether (0°) yields fine yellow needles; m.p. 154°–155°.

(b)
7β-Amino-7α-[(4-methylphenyl)thio]-3-[[(1-methyl-1H-tetrazol-5-yl)thio]methyl]-8-oxo-5-thia-1-azabicyclo-[4.2.0]oct-2-ene-2-carboxylic acid, diphenylmethyl ester 1.32 g. of solid triphenylphosphine is added to a stirred solution of 1.03 g. of 7-[[(4-methylphenyl)thio]-imino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester from part (a) in 100 ml. of methylene chloride at 26° under a nitrogen atmosphere. The mixture is stirred for five hours at 26° at which time TLC indicated the absence of starting material. The reaction mixture is then concentrated under reduced pressure and eluted directly onto a silica gel column. Elution with 5% ethyl acetate/methylene chloride yields 7β-amino-7α-[(4-methylphenyl)thio]-3-[[(1-methyl-1H-tetrazol-5-yl)thio]methyl]-8-oxo-5-thia-1-azabicyclo[4.2.0]oct-2-ene-2-carboxylic acid, diphenylmethyl ester as a nearly colorless, clear oil; PMR (CDCl$_3$) δ 2.00 (Br.S, 2H, exchanged with D$_2$O), 2.30 (S, 3H), 3.60 (S, 2H), 3.76 (S, 3H), 4.26 (d of d, 2H, J = 13), 4.73 (S, 1H), 6.86 (S, 1H), 7.30 (M, 14H); I.R. (CHCl$_3$) 1775, 1715 cm$^{-1}$.

Alternatively, the titled product can be obtained by adding 2 g. of an acidic silica gel (Mallinckrodt Silicar CC-4) followed by 0.44 g. of triphenylphosphine to a stirred solution of 1.03 g. of thiooxime product from part (a) in 50 ml. methylene chloride at 26° under a nitrogen atmosphere. The mixture is stirred at 26° for two hours, at which time TLC indicated the absence of starting material. The reaction mixture is concentrated under reduced pressure to approximately 20 ml. and eluted directly on a silica gel column (Mallinckrodt Silicar CC-7). Elution with 5% ethyl acetate/methylene chloride yields 7β-amino-7α-[(4-methylphenyl)thio]-3-[[(1-methyl-1H-tetrazol-5-yl)thio]methyl]-8-oxo-5-thia-1-azabicyclo-[4.2.0]oct-2-ene-2-carboxylic acid, diphenylmethyl ester as an oil.

EXAMPLE 64

7β-Amino-7α-methylthio-3-[[(1-methyl-1H-tetrazol-5-yl)thio]-methyl]-8-oxo-5-thia-1-azabicyclo[4.2.0]oct-2-ene-2-carboxylic acid, diphenylmethyl ester (a)
7-[(Methylthio)imino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 0.747 g. (9 mmol.) of methylsulfenyl chloride in 15 ml. of dry methylene chloride is added dropwise with stirring under a nitrogen atmosphere to a cold solution (0°) of 2 g. (3 mmol.) of 7β-amino-3-[[(1-methyl-1H-tetrazol-5-yl)-thio]methyl]-8-oxo-5-thia-1-azabicyclo[4.2.0]oct-2-ene-2-carboxylic acid, diphenylmethyl ester in 160 ml. of dry methylene chloride and 16 ml. of propylene oxide also containing 15 g. of crushed molecular sieves (4A). The reaction mixture is stirred and the temperature allowed to rise to 26° over eight hours. The resulting mixture is filtered, and the filtrate is concentrated under reduced pressure to a semi-crystalline solid. Crystallization from methylene chloride/ethyl ether (0°) yields white needles of 7-[(methylthio)imino]-3-[[(1-methyl-1H-tetrazol-5-yl)thio]-methyl]-8-oxo -5-thia-1-azabicyclo[4.2.0]oct-2-ene-2-carboxylic acid, diphenylmethyl ester; m.p. 213°–214°.

(b)
7β-Amino-7α-methylthio-3-[[(1-methyl-1H-tetrazol-5-yl)-thio]methyl]-8-oxo-5-thia-1-azabicyclo[4.2.0]oct-2-ene-2-carboxylic acid, diphenylmethyl ester Treating the thiooxime part from part (a) according to either of the procedures set forth in Example 63(b) one obtains 7β-amino-7α-methylthio-3-[[(1-methyl-1H-tetrazol-5-yl)thio]methyl]-8-oxo-5-thia-1-azabicyclo[4.2.0]oct-2-ene-2-carboxylic acid, diphenylmethyl ester as an oil; PMR (CDCl$_3$) δ 2.30 (Br.S, 2H), exchanged with D$_2$O), 2.33 (S, 3H), 3.66 (S, 2H), 3.83 (S, 3H), 4.36 (M, 2H), 4.78 (S, 1H), 6.90 (S, 1H), 7.33 (M, 10H); I.R. (CDCl$_3$) 1775, 1715 cm$^{-1}$.

EXAMPLE 65

7-[[(4-Methylphenyl)thio]imino]-3-[(acetyloxy)methyl]-8-oxo-5-thia-1-azabicyclo[4.2.0]oct-2-ene-2-carboxylic acid, diphenylmethyl ester Following the procedure of example 63(a) but employing 7β-amino-3-[(acetyloxy)methyl]-8-oxo-5-thia-1-azabicyclo[4.2.0]oct-2-ene-2-carboxylic acid, diphenylmethyl ester as the starting material, one obtains 7-[[(4-methylphenyl)thio]imino]-3-[(acetyloxy)methyl]-8-oxo-5-thia-1-azabicyclo[4.2.0]oct-2-ene-2-carboxylic acid, diphenylmethyl ester following silica gel chromatography as a yellow oil: PMR (CDCl$_3$) δ 1.96 (S, 3H), 2.33 (S, 3H), 3.41 (M. 2H), 4.85 (d of d, 2H, J = 13), 5.26 (S, 1H), 6.91 (S, 1H), 7.28 (M, 14H); I.R. (CHCl$_3$) 1775, 1730, 1720 (sh) cm$^{-1}$.

EXAMPLES 66–87

Following the procedure of example 63(a) but employing the 7β-amino-cephalosporanic acid ester shown below in Col. I and the sulfenyl chloride shown in Col. II, one obtains the thiooxime product shown in Col. III.

| | Col. I | Col. II |
|---|---|---|
| | [structure: H₂N-CH-CH-S-CH₂-C(CH₂X)=C(COOR)-N-C=O bicyclic] | $R_1-S-Cl$ |

Col. III

[structure: $R_1-S-N=$ bicyclic β-lactam with $CH_2X$ and $COOR$]

| Ex. | X | R | $R_1$ |
|---|---|---|---|
| 66 | —H | —CH₂—C₆H₅ | —CH₃ |
| 67 | —O—C(=O)—CH₃ | —CH₂—C₆H₄—OCH₃ | —C₂H₅ |
| 68 | —O—C(=O)—C₂H₅ | —CH₂—C₆H₄—NO₂ | —n-C₃H₇ |
| 69 | —O—C(=O)—NH₂ | —CH₂—CCl₃ | Cl—C₆H₄— |
| 70 | —O—C(=O)—NH₂ | —CH(C₆H₅)₂ | H₃C—C₆H₄— |
| 71 | —H | —Si(CH₃)₃ | 3,5-(H₃C)₂—C₆H₃— |
| 72 | —S-(1-methyltetrazol-5-yl) | —CH₂—CCl₃ | —C₆H₅ |
| 73 | —S-(1-methyltetrazol-5-yl) | —CH₂—C₆H₄—OCH₃ | H₃CO—C₆H₄— |
| 74 | —S-(5-methyl-1,3,4-thiadiazol-2-yl) | —CH₂—C₆H₅ | —CH₃ |
| 75 | —S-(5-methyl-1,3,4-oxadiazol-2-yl) | —t-C₄H₉ | 2-Br—C₆H₄— |
| 76 | —S-(4-methyl-1,3-thiazol-...) | —t-C₄H₉ | —C₂H₅ |

-continued

| | Col. I | Col. II |
|---|---|---|
| | (structure with H$_2$N, S, CH$_2$, N, C-CH$_2$X, COOR) | R$_1$—S—Cl |
| | Col. III | |
| | (structure with R$_1$—S—N=, S, CH$_2$, N, C-CH$_2$X, COOR) | |

| Ex. | X | R | R$_1$ |
|---|---|---|---|
| 77 | -S-(thiadiazole) | -CH(phenyl)$_2$ | -t-C$_4$H$_9$ |
| 78 | -S-(isothiazole with H$_3$C) | -CH$_2$CCl$_3$ | H$_5$C$_2$-(phenyl)- |
| 79 | -S-(isoxazole with CH$_3$) | -CH$_2$OCH$_3$ | -CH$_3$ |
| 80 | -S-(triazole with N-CH$_3$) | -CH(phenyl)$_2$ | -(phenyl) |
| 81 | -H | -CH$_3$ | -CH$_3$ |
| 82 | -O-C(=O)-CH$_3$ | -CH$_2$-O-C(=O)-C(CH$_3$)$_3$ | H$_3$C-(phenyl)- |
| 83 | -S-(tetrazole with N-CH$_3$) | -i-C$_3$H$_7$ | H$_3$C-(phenyl)- |
| 84 | -S-(tetrazole with N-CH$_3$) | (phthalidyl structure) | H$_3$C-(phenyl)- |
| 85 | -S-(tetrazole with N-CH$_3$) | -CH(CH$_3$)-O-C(=O)-C(CH$_3$)$_3$ | -CH$_3$ |
| 86 | -O-C(=O)-CH$_3$ | -CH(CH$_3$)-O-C(=O)-CH$_3$ | -CH$_3$ |
| 87 | -S-(tetrazole with N-CH$_3$) | -CH$_2$-O-C(=O)-C(CH$_3$)$_3$ | -CH$_3$ |

The thiooxime products of examples 66 to 87 can then be reacted according to either of the procedures of example 63(b) to yield the corresponding 7β-amino-7α-substituted thiocephalosporanic acid ester.

EXAMPLES 88–96

Following the procedure of example 63(a) but employing the 7β-amino cephalosporanic acid ester shown below in Col. I and the sulfenyl chloride shown in Col.

II, one obtains the thiooxime product shown in Col. III.

| Ex. | Col. I (R) | Col. II (R₁—S—Cl) |
|---|---|---|
| 88 | —CH₂—C₆H₅ | —CH₃ |
| 89 | —CH(C₆H₅)₂ | H₃C—C₆H₄— |
| 90 | —CH₂—C₆H₄—NO₂ | —C₆H₅ |
| 91 | —CH₂—C₆H₄—OCH₃ | Cl—C₆H₄— |
| 92 | —Si(CH₃)₃ | H₃CO—C₆H₄— |
| 93 | —CH₂—CCl₃ | —C₂H₅ |
| 94 | —CH(CH₃)—O—C(O)—C₂H₅ | —CH₃ |
| 95 | —CH₂—O—C(O)—C(CH₃)₃ | H₃C—C₆H₄— |
| 96 | phthalidyl | —CH₃ |

The thiooxime products of examples 88 to 96 can be reacted according to either of the procedures of example 63(b) to yield the corresponding 7β-amino-7α-substituted thio cephalosporanic acid ester.

EXAMPLES 97–110

Following the procedure of example 63(a) but employing the 7β-amino cephalosporanic acid ester shown below in Col. I and the sulfenyl chloride shown in Col. II, one obtains the thiooxime product shown in Col. III.

| Ex. | Col. I (R) | Y | Col. II (R₁) |
|---|---|---|---|
| 97 | —CH₂—C₆H₅ | Cl | H₃C—C₆H₄— |
| 98 | —CH(C₆H₅)₂ | Cl | —CH₃ |
| 99 | —CH₂—C₆H₄—NO₂ | Br | —C₂H₅ |
| 100 | —CH₂—C₆H₄—OCH₃ | F | —C₆H₅ |
| 101 | —CH₂CCl₃ | I | H₃CO—C₆H₄— |
| 102 | —CH₂—O—C(O)—C(CH₃)₃ | Cl | —CH₃ |
| 103 | —CH—O—C(O)—C(CH₃)₃ | Cl | H₃C—C₆H₄— |
| 104 | phthalidyl | Cl | —CH₃ |
| 105 | phthalidyl | —OCH₃ | H₃C—C₆H₄— |
| 106 | —Si(CH₃)₃ | —OC₂H₅ | —CH₃ |
| 107 | —CH(C₆H₅)₂ | —OCH₃ | —C₆H₅ |
| 108 | —CH₂—C₆H₄—OCH₃ | —OCH₃ | Cl—C₆H₄— |
| 109 | —CH₂CCl₃ | —OC₂H₅ | —C₂H₅ |
| 110 | —CH₂OCH₃ | —OCH₃ | H₃C—C₆H₄— |

The thiooxime products of examples 97 to 110 can be reacted according to either of the procedures of example 63(b) to yield the corresponding 7β-amino-7α-substituted thio cephalosporanic acid ester.

EXAMPLE 111

6β-Amino-6α-[(4-methylphenyl)thio]-3,3-dimethyl-7-oxo-4-thia-1-azabicyclo[3.2.0]heptane-2-carboxylic acid, 2,2,2-trichloroethyl ester (a)

6-[[(4-Methylphenyl)thio]imino]-3,3-dimethyl-7-oxo-4-thia-1-azabicyclo[3.2.0]heptane-2-carboxylic acid, 2,2,2-trichloroethyl ester 0.262 ml. (1.88 mmol.) of triethylamine is added dropwise under a nitrogen atmosphere to a cold (0°) mixture of 1 g. (1.88 mmol.) of 6β-amino-3,3-dimethyl-7-oxo-4-thia-1-azabicyclo[3.2.0]heptane-2-carboxylic acid, 2,2,2-trichloroethyl ester p-toluenesulfonate salt in 80 ml. of dry methylene chloride and 8 ml. of propylene oxide also containing 10 g. of crushed molecular sieves (4A). After the addition is completed, 0.9 g. (5.64 mmol.) of p-toluenesulfenyl chloride is added dropwise with stirring. The reaction mixture is stirred at 0° for two hours and at 26° for 30 minutes. The resulting mixture is filtered and the filtrate is evaporated to dryness under reduced pressure. Chromatography on a silica gel column (Mallinckrodt Silicar CC-7) (methylene chloride) yields 6-[[(4-methylphenyl)-thio]imino]-3,3-dimethyl-7-oxo-4-thia-1-azabicyclo[3.2.0]-heptane-2-carboxylic acid, 2,2,2-trichloroethyl ester as a clear, bright yellow oil; PMR (CDCl$_3$) δ 1.60 (Br.S, 6H), 2.36 (S, 3H), 4.73 (S, 1H), 4.80 (S, 2H), 5.73 (S, 1H), 7.33 (d of d, 4H); I.R. (CHCl$_3$) 1780, 1760 (Sh) cm$^{-1}$; U.V. (MeOH) 226 mμ (ε 8,300), 267 mμ (ε 3,600), 338 mμ (ε 3,600); mass spectrum m/e 466 (M$^+$).

(b)

6β-Amino-6α-[(4-methylphenyl)thio]-3,3-dimethyl-7-oxo-4-thia-1-azabicyclo[3.2.0]heptane-2-carboxylic acid, 2,2,2-trichloroethyl ester The thiooxime product from part (a) is reacted with triphenylphosphine according to the second procedure set forth in Example 63(b) to yield 6β-amino-6α-[(4-methylphenyl)-thio]-3,3-dimethyl-7-oxo-4-thia-1-azabicyclo[3.2.0]heptane-2-carboxylic acid, 2,2,2-trichloroethyl ester as an oil: PMR (CDCl$_3$) δ 1.55 (S, 3H), 1.63 (S, 3H), 2.36 (S, 5H, 3H after D$_2$O exchange), 4.55 (S, 1H), 4.76 (S, 2H), 5.50 (S, 1H), 7.30 (d of d, 4H, J = 8); I.R. (CHCl$_3$) 1780, 1770 (Sh) cm$^{-1}$; mass spectrum m/e 468 (M$^+$).

EXAMPLE 112

6α-Methoxy-6β-[(phenylacetyl)amino]-3,3-dimethyl-7-oxo-4-thia-1-azabicyclo[3.2.0]heptane-2-carboxylic acid, 2,2,2-trichloroethyl ester 16.1 g. (34.54 mmol.) of the thiooxime product from example 111(a) and 27.66 g. (103.6 mmol.) of triphenylphosphine are dissolved in 600 ml. of methylene chloride at 26°. A solution of 11.02 g. of mercuric acetate in 150 ml. of methanol is immediately added and the reaction mixture is allowed to stir for 3.5 hours. The reaction mixture is evaporated to dryness under reduced pressure and then redissolved in 600 ml. of methylene chloride and 150 ml. of propylene oxide. This solution is chilled to −10° and a solution of 25.8 g. of phenylacetylchloride in 80 ml. of methylene chloride is added dropwise with stirring. After three hours, the reaction mixture is concentrated to an oil and chromatographed on silica gel (Mallinckrodt Silicar CC-7). 6α-Methoxy-6β-[(phenacetyl)amino]-3,3-dimethyl-7-oxo-4-thia-1-azabicyclo-[3.2.0]heptane-2-carboxylic acid, 2,2,2-trichloroethyl ester is isolated as a clear oil: NMR (CDCl$_3$) δ 1.40 (S, 3H), 1.46 (S, 3H), 3.40 (S, 3H), 3.63 (S, 2H), 4.51 (S, 1H), 4.81 (S, 2H), 5.66 (S, 1H), 7.30 (S, 5H).

EXAMPLE 113

6-[(Methylthio)imino]-3,3-dimethyl-7-oxo-4-thia-1-azabicyclo-[3.2.0]heptane-2-carboxylic acid, 2,2,2-trichloroethyl ester Methylsulfenyl chloride is reacted with 6β-amino-3,3-dimethyl-7-oxo-4-thia-1-azabicyclo[3.2.0]heptane-2-carboxylic acid, 2,2,2-trichloroethyl ester p-toluenesulfonate salt according to the procedure of Example 111(a) and yields without chromatography a crystalline solid. Recrystallization of this crude product from methylene chloride/hexane yields white crystalline 6-[(methylthio)imino]-3,3-dimethyl-7-oxo-4-thia-1-azabicyclo[3.2.0]heptane-2-carboxylic acid, 2,2,2-trichloroethyl ester; m.p. 129°–130°.

EXAMPLES 114–132

Following the procedure of example 111 but employing the 6β-amino-penicillanic ester shown in Col. I and the sulfenyl chloride shown in Col. II, one obtains the thiooxime product shown in Col. III.

| | Col. I | Col. II |
|---|---|---|
| | (6β-amino penicillanic ester, R group varies) | R$_1$—S—Cl |
| | Col. III | |
| | (thiooxime product) | |
| Ex. | R | R$_1$ |
| 114 | —CH$_3$ | phenyl |
| 115 | —C$_2$H$_5$ | 4-methoxyphenyl (H$_3$CO—C$_6$H$_4$—) |
| 116 | —n-C$_3$H$_7$ | —C$_2$H$_5$ |
| 117 | —t-C$_4$H$_9$ | —CH$_3$ |
| 118 | —t-C$_4$H$_9$ | 4-methoxyphenyl (H$_3$CO—C$_6$H$_4$—) |
| 119 | —Si(CH$_3$)$_3$ | 2-chlorophenyl |
| 120 | —CH$_2$—C$_6$H$_5$ | —CH$_3$ |
| 121 | —CH$_2$—C$_6$H$_4$—NO$_2$ | —C$_2$H$_5$ |

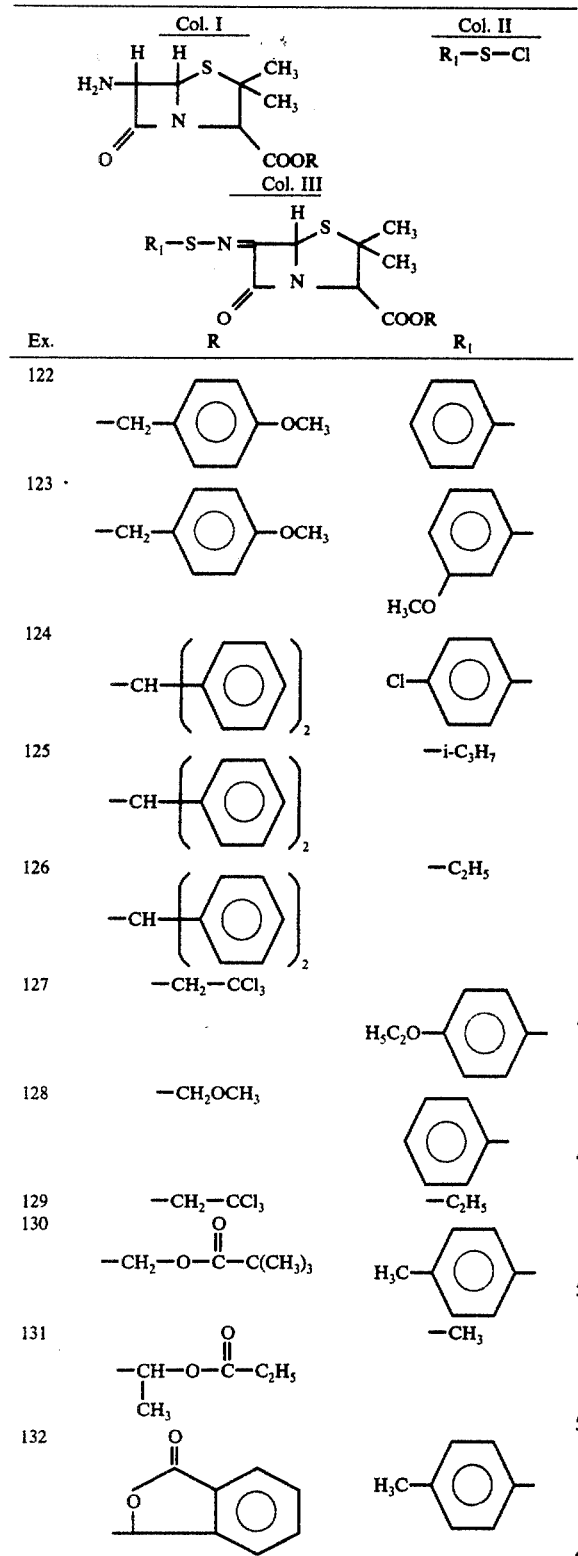

The thiooxime products from examples 113 to 132 can be reacted as taught in either example 111(b) or example 112 to yield the corresponding 6β-amino-6α-substituted thio penicillanic acid ester or acylated 6α-methoxy penicillanic acid ester.

EXAMPLE 133

7β-Amino-7α-methoxy-3-[[(1-methyl-1H-tetrazol-5-yl)thio]-methyl]-8-oxo-5-thia-1-azabicyclo[4.2.0]oct-2-ene-2-carboxylic acid, diphenylmethyl ester 0.264 g. (1 mmol.) of triphenylphosphine is added to a stirred solution of 0.206 g. (0.33 mmol.) 7-[[(4-methyl-phenyl)thio]imino]-3-[[(1-methyl-1H-tetrazol-5-yl)-thio]methyl]-8-oxo-5-thia-1-azabicyclo[4.2.0]oct-2-ene-2-carboxylic acid, diphenylmethyl ester from example 63(a) in 20 ml. of methylene chloride at 26° under a nitrogen atmosphere. The mixture is stirred at 26° for 12 hours and then 0.106 g. (0.33 mmol.) of mercuric acetate in 5 ml. of methanol is added. After two hours, the mixture is concentrated and ether is added precipitating out the desired 7β-amino-7α-methoxy-3-[[(1-methyl-1H-tetrazol-5-yl)-thio]methyl]-8-oxo-5-thia-1-azabicyclo[4.2.0]oct-2-ene-2-carboxylic acid, diphenylmethyl ester.

Alternatively, the triphenylphosphine, the thiooxime compound from example 63(a), the methylene chloride, the mercuric acetate, and the methanol in the amounts set forth above are mixed together at one time. After five hours, the mixture is concentrated and ether is added precipitating out the desired 7β-amino-7α-methoxy-3-[[(1-methyl-1H-tetrazol-5-yl)thio]methyl]-8-oxo-5-thia-1-azabicyclo-[4.2.0]oct-2-ene-2-carboxylic acid, diphenylmethyl ester.

EXAMPLE 134

7β-[(Phenylacetyl)amino]-7α-methoxy-3-[[(1-methyl-1H-tetrazol-5-yl)thio]methyl]-8-oxo-5-thia-1-azabicyclo[4.2.0]-oct-2-ene-2-carboxylic acid, diphenylmethyl ester A reaction mixture of 0.264 g. (1 mmol.) of triphenylphosphine, 0.206 g. (0.33 mmol.) of 7-[[(4-methyl-phenyl)-thio]imino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester from example 63(a), 20 ml. of methylene chloride, 0.106 g. (0.33 mmol.) of mercuric acetate, and 5 ml. of methanol is prepared as set forth in the alternate procedure of example 133. After five hours, the mixture is evaporated to dryness under reduced pressure. The residue is taken up in 25 ml. of methylene chloride and 5 ml. of propylene oxide. This solution is chilled to −10° and from 5 to 10 equivalents of phenylacetylchloride is added dropwise with stirring. After 3.5 hours, the mixture is concentrated to an oil. Chromatography on silica gel (Mallinckrodt Silicar CC-7) affords 7β-[[phenylacetyl]amino]-7α-methoxy-3-[[(1-methyl-1H-tetrazol-5-yl)thio]-methyl]-8-oxo-5-thia-1-azabicyclo[4.2.0]oct-2-ene-2-carboxylic acid, diphenylmethyl ester as an oil: NMR (CDCl$_3$) δ 3.46 (S, 3H), 3.50 (S, 2H), 3.66 (S, 2H), 3.83 (S, 3H), 4.36 (d, 2H, J = 9 Hz), 5.00 (S, 1H), 6.33 (Br.S, 1H), 6.90 (S, 1H), 7.33 (S, 15H).

EXAMPLE 135

The inhibition of a β-lactamase enzyme by the thiooxime compounds of examples 1 to 3 is demonstrated by the following procedure.

Two plates having a 350 ml. agar base are prepared. In one plate labeled "control", 150 ml. of agar seeded with 1 ml. of *Micrococcus luteus* SC2495 is added. To the second plate labeled "inhibitor plate", 150 ml. of agar containing 1 ml. of *Micrococcus luteus* SC2495, 0.3 μg./ml. of cephradine and 0.13 units/ml. of cephradinase (a β-lactamase enzyme) is added. It had previously been determined that this amount of cephradinase would inactivate the cephradine and allow the *Micrococcus luteus* to grow. The compounds to be tested are then disced on both plates and the zones of inhibition are compared.

| Compound | Zone of inhibition (mm.) | |
|---|---|---|
| | Control Plate | Inhibition Plate |
| Product of Ex. 1 | 0 | 40 |
| Product of Ex. 2 | 0 | 30 |
| Product of Ex. 3 | 0 | 37 |

Thus, the thiooximes of examples 1 to 3 while not active themselves against *Micrococcus luteus* did inhibit the cephradinase.

What is claimed is:

1. A compound of the formula:

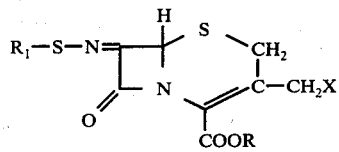

wherein R is hydrogen, lower alkyl of 1 to 4 carbons, benzyl, p-methoxybenzyl, p-nitrobenzyl, diphenylmethyl, 2,2,2-trichloroethyl, tri(lower alkyl) silyl, lower alkoxymethyl,

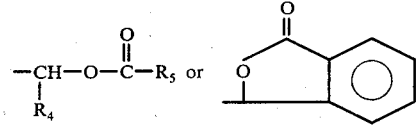

X is hydrogen,

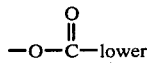

alkyl wherein alkyl is of 1 to 4 carbons,

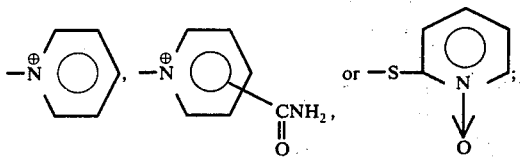

$R_1$ is lower alkyl of 1 to 4 carbons, phenyl, or phenyl having a halo, lower alkyl of 1 to 4 carbons, or lower alkoxy of 1 to 4 carbons substituent; $R_4$ is hydrogen or lower alkyl of 1 to 4 carbons; and $R_5$ is lower alkyl of 1 to 4 carbons.

2. The compound of claim 1 wherein X is hydrogen,

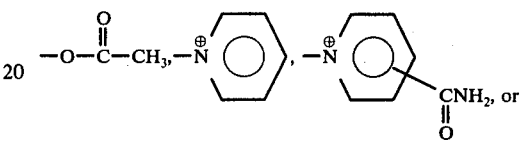

$R_1$ is lower alkyl of 1 to 4 carbons, phenyl, or phenyl having a Cl, Br, methyl, ethyl, methoxy or ethoxy substituent; $R_4$ is hydrogen or methyl; and $R_5$ is $-C(CH_3)_3$.

3. The compound of claim 2 wherein X is

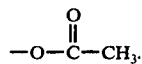

4. The compound of claim 3 wherein $R_1$ is methyl.
5. The compound of claim 4 wherein R is hydrogen.
6. The compound of claim 4 wherein R is diphenylmethyl.
7. The compound of claim 3 wherein $R_1$ is 4-methylphenyl.
8. The compound of claim 7 wherein R is hydrogen.
9. The compound of claim 7 wherein R is diphenylmethyl.
10. The compound of claim 2 wherein X is hydrogen.
11. The compound of claim 10 wherein $R_1$ is 4-methylphenyl.
12. The compound of claim 11 wherein R is hydrogen.

* * * * *

UNITED STATES PATENT AND TRADEMARK OFFICE
CERTIFICATE OF CORRECTION

PATENT NO. : 4,109,084
DATED : August 22, 1978
INVENTOR(S) : ERic M. Gordon

It is certified that error appears in the above-identified patent and that said Letters Patent are hereby corrected as shown below:

Col. 3, the second structure at line 1 should read as follows:

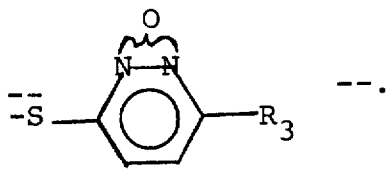

Col. 7, line 39, insert -- ∿ -- before "1000".

The structure (Col. I) at Col. 8, line 20 should read:

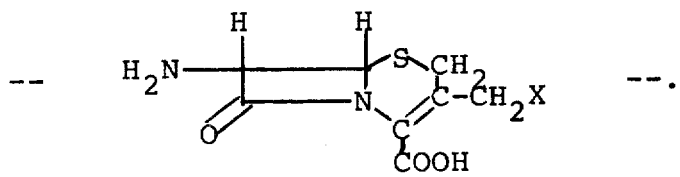

Col. 8, the structure of Col. III at line 25 should read:

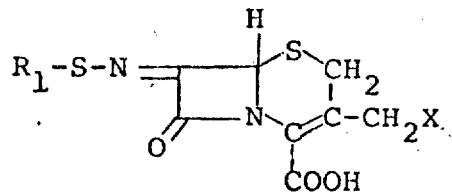

UNITED STATES PATENT AND TRADEMARK OFFICE
CERTIFICATE OF CORRECTION

PATENT NO. : 4,109,084
DATED : August 22, 1978
INVENTOR(S) : Eric M. Gordon

It is certified that error appears in the above—identified patent and that said Letters Patent are hereby corrected as shown below:

Col. 9, the structure of Col. I at line 1 should read:

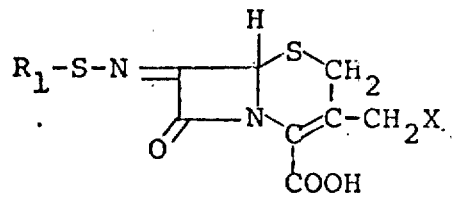

Col. 9, the structure of Col. 3 should read

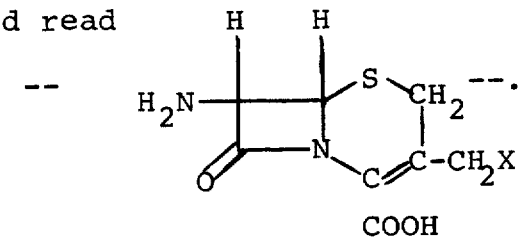

Signed and Sealed this

Tenth Day of July 1979

[SEAL]

Attest:

*Attesting Officer*

LUTRELLE F. PARKER
*Acting Commissioner of Patents and Trademarks*